Figure 2A:
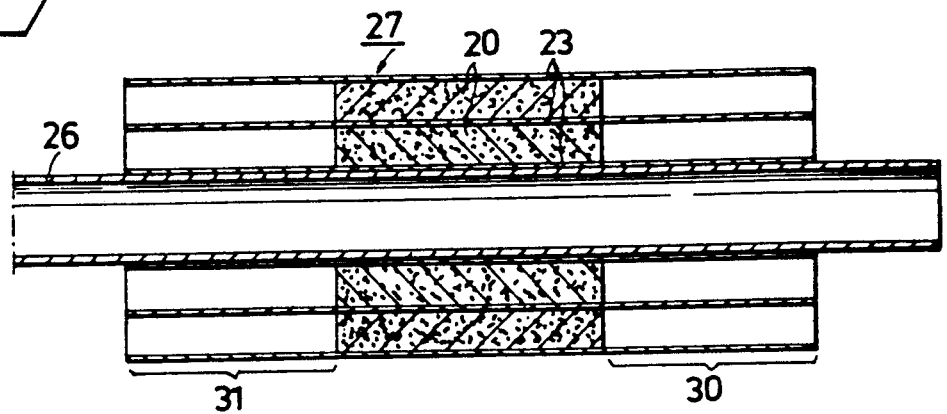

United States Patent [19]

Hodén et al.

[11] Patent Number: 5,019,061
[45] Date of Patent: May 28, 1991

[54] TAMPON AND A METHOD FOR ITS MANUFACTURE

[75] Inventors: Ebbe Hodén, Mariefred, Sweden; Maja Mokvist, Snellville, Ga.

[73] Assignee: AB Bergasa Industrier, Mariefred, Sweden

[21] Appl. No.: 472,176

[22] Filed: Jan. 30, 1990

[30] Foreign Application Priority Data

May 30, 1989 [SE] Sweden ................... 8901936

[51] Int. Cl.⁵ ............. A61F 13/15; A61F 13/20
[52] U.S. Cl. ................. 604/358; 604/385.1; 604/904
[58] Field of Search ............... 156/313, 446, 516, 519, 156/194; 604/358, 379, 385.1, 904

[56] References Cited

U.S. PATENT DOCUMENTS

| | | | |
|---|---|---|---|
| 3,854,481 | 12/1974 | Messing | 604/904 X |
| 3,919,028 | 11/1975 | Lewis et al. | 156/313 X |
| 4,642,108 | 2/1987 | Sustmann | 604/358 X |
| 4,816,100 | 3/1989 | Friese | 604/904 X |
| 4,859,273 | 8/1989 | Friese | 156/446 X |
| 4,863,450 | 9/1989 | Friese | 604/379 X |
| 4,900,383 | 2/1990 | Dursch et al. | 156/190 X |

Primary Examiner—Alan Cannon
Assistant Examiner—Elizabeth M. Burke
Attorney, Agent, or Firm—Fleit, Jacobson, Cohn, Price, Holman & Stern

[57] ABSTRACT

A tampon comprises a compacted tampon blank, which in turn is formed by winding a liquid-permeable strip and a string of absorbent material placed thereon to a roll and inserting strip-parts which project from the sides of the string, inwardly of the innermost turn or winding of the roll. In the process of manufacturing the tampon, the strip carrying the string can be wound around a first, tubular mandrel, and one strip-part can be inserted into the mandrel through one open mandrel-end located adjacent the inner edge of the strip-part. A second tubular mandrel is then inserted through the open end of the first mandrel and the first mandrel then withdrawn. With the second mandrel surrounded by the first, inserted strip-part and located with an open end adjacent the inner edge of the other strip-part, the other strip-part is inserted into the second mandrel, which is then withdrawn from the thus formed tampon blank, which is thereafter compacted or compressed.

15 Claims, 2 Drawing Sheets

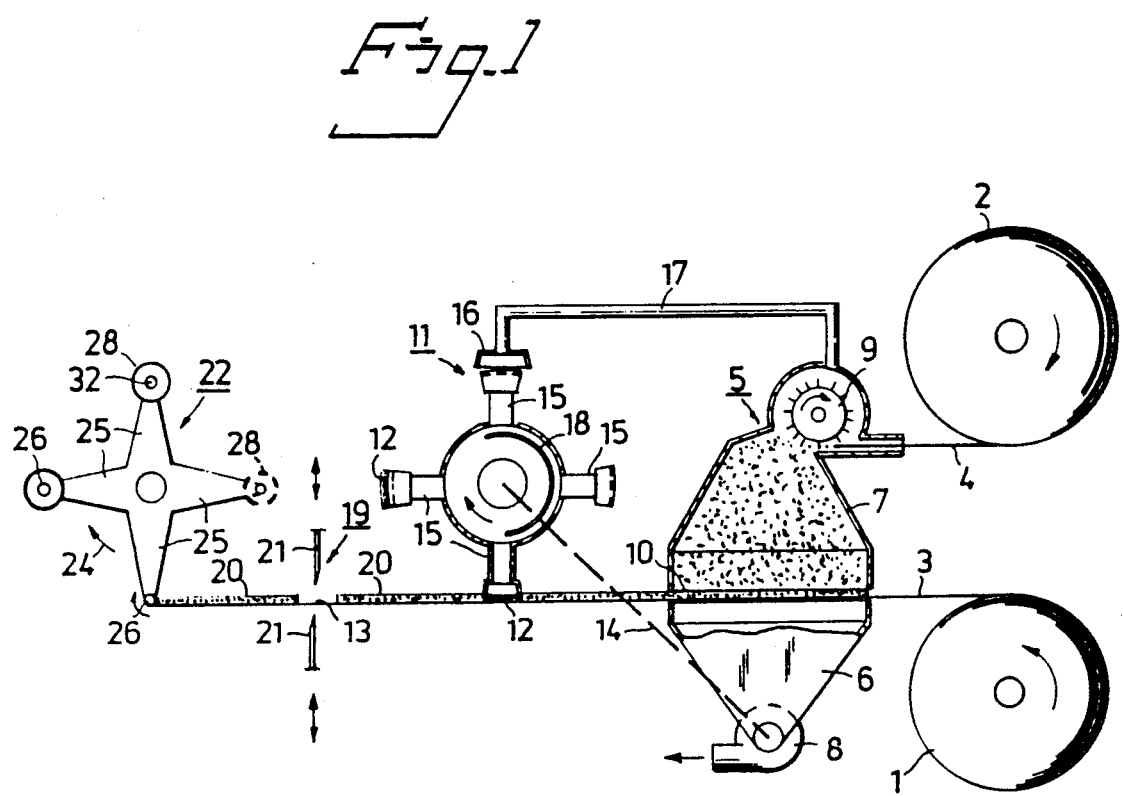

TAMPON AND A METHOD FOR ITS MANUFACTURE

The present invention relates to an improved tampon, particularly a menstruation tampon, of the kind comprising a body of substantially cylindrical external shape and obtained by winding an elongated starting-blank formed from a strip of thin, liquid-permeable layer material having a largest width greater than the length of the tampon and a string of absorbent material placed on the strip substantially symmetrically in relation to the longitudinal axis of said strip and having a width which corresponds substantially to the length of the tampon, several turns around a mandrel which extends transversely to the longitudinal direction of the blank, therewith to form a roll, and compressing the roll predominantly in its radial direction. The invention also relates to a method for the manufacture of the improved tampon.

An object of the present invention is to provide a novel and advantageous tampon whose construction enables the absorbent filling of the tampon to be selected from a wide choice of materials, for example so that a highly absorbent filling material which has little or substantially negligible self-cohesion can be used in the tampon in a problem-free manner.

To this end, there is proposed in accordance with the invention a tampon of the kind described in the introduction, wherein said turns comprise single layers of said strip with a filling formed from the string of absorbent material located between said layers and wherein such edge parts of the layer-material strip which in the wound state of the blank extend externally to both sides of the string are twisted inwardly and accommodated in a space located inwardly of the innermost turn.

As before mentioned, a further object of the invention is to provide a novel and advantageous tampon-manufacturing method, this method comprising forming a tampon blank in the form of a body having a substantially cylindrical external configuration and containing a filling of absorbent material enclosed in a casing of thin, liquid-permeable layer material, and compacting the tampon blank to its final tampon form, and in which method the absorbent material forming said filling is applied in the form of a string which has a width which corresponds at least substantially to the length of the finished tampon onto a strip of said layer material which has a greatest width exceeding the width of the string, said string being placed on the strip at least substantially symmetrically with the longitudinal centre line of said strip, wherein;

the strip of layer material having located thereon the string of absorbent material, for forming said tampon blank, is coiled onto a first tubular mandrel with said string located on the side of the strip facing towards said mandrel; a part of the strip projecting from one side of the string with the end of the mandrel located adjacent the inner edge of said part is inserted into the interior of said first mandrel; and a second tubular mandrel is inserted through said mandrel end of the first mandrel in a manner such as to be surrounded by the layer-material part inserted into said first mandrel; the first mandrel is then completely withdrawn;

a part of the strip projecting out from the string on the other side, with the end of the second mandrel located adjacent the inner end of said part, is inserted into the interior of the second mandrel; and the second mandrel is then fully withdrawn prior to compacting the tampon blank thus formed to its final tampon form.

Further characterizing features of the invention are set forth in the depending claims, whereas further advantages afforded by the invention will be apparent from the following description made with reference to the accompanying drawings, in which;

FIG. 1 illustrates highly schematically an exemplifying embodiment of a machine for manufacturing tampons in accordance with the invention; and FIG. 2a–d illustrate highly schematically the various stages in the manufacture of a tampon in accordance with the invention.

The reference numerals 1 and 2 in FIG. 1 identify storage reels comprising respectively thin strip-like liquid-permeable layer material and strip-like starting material for an absorbent-filling enclosed in the layer material in tampons produced by the illustrated machine. Webs 3 and 4 of the layer material and the tampon-filling starting material are drawn from respective reels 1, 2, preferably continuously, with the reels rotating in the direction shown by the arrows. The web 3 of layer material may advantageously consist of a nonwoven material, such as nonwoven gauze, and the web 4 forming the starting material for the tampon filling is here presumed to consist of a suitable paper pulp, so-called fluff pulp. The web 3 is conveyed through the machine while resting on an endless thread belt (not shown) or some like device and is passed to a first station 5 comprising an upper hood 7 and a lower hood 6. The hood 6 is connected at the bottom thereof to the suction side of a fan 8, and a shredder or defibrator 9 is connected to the top of the hood 7. When seen at right angles to the plane of the drawing, the hoods 6 and 7 have a width which is smaller than the width of the web 3, preferably less than half the width of said web 3. The fan 8 is operative to generate a subpressure in the hood 6, so that the discrete pulp-fibres produced in the defibrator 9 will be sucked firmly against the web 3, to form a fibre string 10 of high absorbency, which accompanies the web 3 out of the station 5.

The reference 11 identifies generally a suction station in which parts 12 of the fibre-string 10 are removed from the string by suction at uniform intervals, such as to leave parts 13 on the web 3 which are devoid of fibre material formed from the reel 2. The suction station has the form of a hollow wheel which rotates in the direction of the arrow shown and the interior of which is connected to a subpressure source, for instance to the suction side of the fan 8, as indicated by the broken line 14. The wheel is provided with radially extending, hollow arms 15, the outer ends of which a perforated and move at a peripheral speed which coincides with the speed at which the web 3 and the string 10 move from the right to the left in FIG. 1. The string-parts 12 entrained by the arms 15 are sucked through a hood 16 as the arms pass said hood. The hood 16 is connected to the hood 7 in the station 5 via a conduit 17 and the defibrator 9. In the illustrated embodiment, there is provided a stationary shielding plate 18 which will ensure that a sub-pressure will prevail at the outer, perforated ends of the arms 15 solely while the arms move from the lowermost position of their rotating cycle to a position immediately before the hood 16.

The web 3 is cut at the location of the empty web-parts 13 in a web-cutting station 19 located downstream of the station 11, such as to separate the web 3 between the residual string-parts 20 located thereon. Cutting of the web is effected by means of two mutually coacting cutters 21 which move reciprocatingly in the direction of the arrows shown.

The machine includes a terminal station 22, in which the Web-pieces or strips 23 (FIGS. 2a–d) separated in the cutting station 19 together with the loose-fibre string-parts 20 carried thereon are wound onto rotatable first hollow mandrels 26 which are displaceable in the direction of their longitudinal axis, i.e. in a direction perpendicular to the plane of the drawing in FIG. 1. These mandrels 26 are attached to the outer ends of arms 25 which extend radially outwards from a hub part of a wheel which rotates intermittently in the direction of arrow 24. In the lowermost position in the station 22, the mandrels 26 rotate clockwise in the manner indicated by an arrow, and the peripheral speed of the mandrel 26 or the strip 23 carrying the string-part 20 rolled thereon exceeds the speed of the web 3, so as to create a distance between the rearward end of the strip being wound and the forward end of the next-following strip. This arrangement enables the wheel carrying said arms 25 to rotate one-quarter of a revolution at a time in the direction of the arrow 24, thereby enabling a fresh mandrel 26 to be brought to the lowermost position in readiness for receiving and winding each newly arriving strip 23 carrying a string-part 20.

Thus, in the first or lowermost mandrel position in the station 22, a strip 23 carrying a string-part 20 is wound onto a hollow, rotatable mandrel to form a roll or cylinder 27 having the configuration illustrated in FIG. 1a. Subsequent to rotating through 90° to a second position and through 180° to a third position, the first and the second ends of the roll 27 are treated in the manner illustrated in FIGS. 2b and 2c. Subsequent to rotating through 270° to a fourth position, the finished tampon blank is removed from the station 22, this tampon blank being shown in broken lines at 28 in FIG. 1 and in FIG. 2c. The tampon blank is then compressed, predominantly in a radial direction, in a conventional manner (for example in accordance with SE Patent Specification 8800774-5, FIG. 2) to form a finished tampon 29, illustrated in FIG. 2d.

The roll or cylinder 27 illustrated in FIG. 2a comprises two turns or windings of the string 20 of absorbent filling material, these turns being separated or covered respectively by three turns of the strip 23 of liquid-permeable layer material. The string 20 of filling material has a width which corresponds essentially to the length of the finished tampon shown in FIG. 2d. The tubular mandrel 26 extends from the left in FIG. 2a, completely through the roll 27, including the parts 30 and 31 of the strip 23 projecting from both sides of the string 20.

Figure 2B:
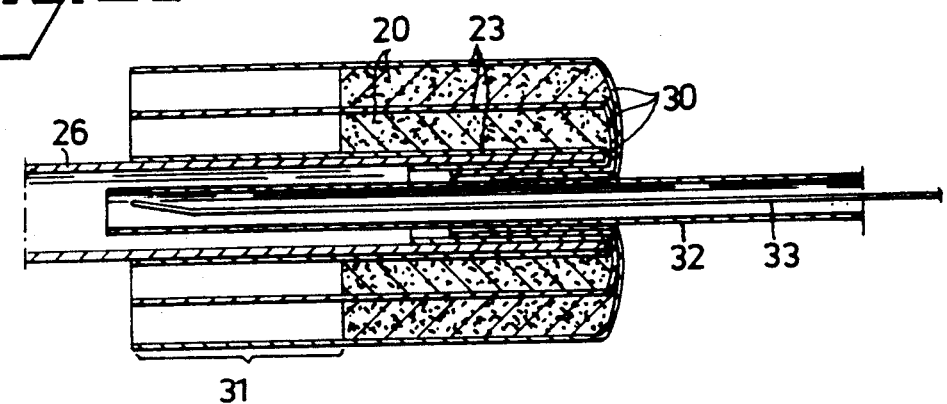

FIG. 2b corresponds to the aforesaid second mandrel position in station 22 in FIG. 1. In this position, the mandrel 26 has been withdrawn so that its forward end terminates at the inner edge of the strip-part 30, and this strip-part 30 has been inserted into the interior of the mandrel 26 together with or by means of a second tubular mandrel 32 whose outer diameter is smaller than the inner diameter of the mandrel 26 such as to provide space between the mandrels 26, 32 for accommodation of the inserted strip-part 30 and such that said strip-part will surround the second mandrel 32. The second mandrel 32 is inserted into the first mandrel 26 from the right in FIG. 2b, and a withdrawal thread 33 is inserted into the second mandrel 32, the end of the second mandrel and the end of the thread 33 being located in the proximity of the outer edge of the strip-part 31.

Figure 2C:
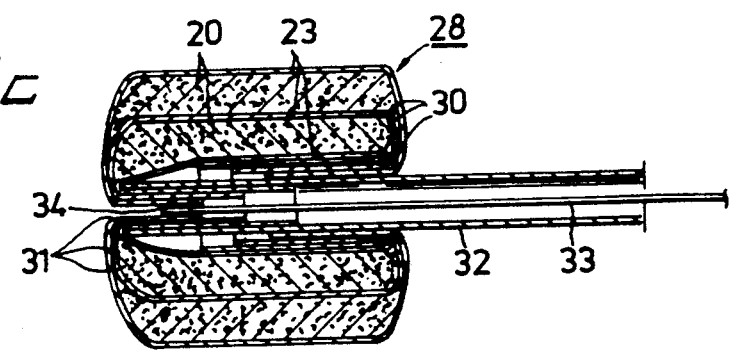
Figure 2D:
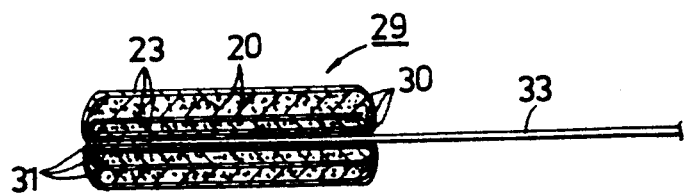

FIG. 2c corresponds to the said third position in the station 22 in FIG. 1, in which the mandrel 26 has been fully withdrawn and the second mandrel 32 has been drawn back to a position in which its forward end is located adjacent the inner edge of the strip-part 31. Furthermore, the outer end of the withdrawal thread 33 has been connected at 34 to the strip-part 31, and the strip-part 31 has been inserted, e.g. by means of a third mandrel (not shown), or by means of the withdrawal thread 33 into the second mandrel 32. The tampon blank 28 formed in accordance with FIG. 2c is removed from the second mandrel 32 (in the fourth position in the station 22 in the FIG. 1) and is compressed or compacted in a conventional manner, to form the finished tampon illustrated in FIG. 2d. It will be seen that the illustrated construction of the tampon 29 and the illustrated method of attachment of the withdrawal thread 33 prevents effectively axial movement of the winding turns relative to one another, and that a filling 20 of highly-absorbent, discrete particles or fibres, which otherwise have the tendency to lump together locally, is effectively reinforced and prevented from forming agglomerates by the illustrated arrangement of the strip 23, which may itself consist of a material of low absorbency or a totally inabsorbent material. As a result of the illustrated arrangement, there is obtained circumferential passages of substantially uniform thickness e filled by the filling material 20, which is a highly advantageous pattern from the aspect of absorption.

It will be understood that the invention is not restricted to the illustrated and described embodiment, and that modifications can be made within the scope of the inventive concept defined in the following claims. For example, the filling 20 may comprise more than one material and may consist initially of loose absorbent particles and/or fibres. Furthermore, the layer material may be composed of more than one web and the web or webs may have widths which vary along their respective lengths, such that the width of the forward ends of the strips 23 corresponds to the width of the string 20, whereas the width of the rear ends of the strips 23 have a width considerably greater than the width of the string 20.

We claim:

1. A tampon, comprising a body of substantially cylindrical external shape and obtained by winding an elongated starting-blank formed from a strip of thin, liquid-permeable layer material having a largest width greater than the length of the tampon and a string of absorbent material placed on the strip substantially symmetrically in relation to the longitudinal axis of said strip and having a width which corresponds substantially to the length of the tampon, several turns around a mandrel which extends transversely to the longitudinal direction of the blank, therewith to form a roll, and compressing the roll predominantly in its radial direction, wherein said turns comprise single layers of said strip with a filling formed from the string of absorbent material located between said layers and wherein such edge parts of the layer-material strip which in the wound state of the blank extend externally to both sides of the string are twisted inwardly and accommodated in a space located inwardly of the innermost turn.

2. A tampon according to claim 1, wherein said string is comprised at least partially of discrete particles or fibres of absorbent material.

3. A tampon according to claim 2, wherein at least an essential part of said absorbent material consists of defibrated paper pulp or fluff pulp.

4. A tampon according to claim 3, wherein said pulp is unbleached.

5. A tampon according to claim 1, wherein said string terminates at a distance from at least one end of the layer-material strip.

6. A tampon according to claim 1, wherein one end part of a withdrawal thread extends in through one end of the tampon surrounded by the inwardly twisted strip-part at said end and is fastened to the strip-part inwardly twisted at the opposite end of the tampon and located in the tampon inwardly of the innermost turn.

7. A method for manufacturing a tampon, comprising forming a tampon blank in the form of a body having a substantially cylindrical external configuration and containing a filling of absorbent material enclosed in a casing of thin, liquid-permeable layer material, and compacting the tampon blank to its final tampon form, and in which method the absorbent material forming said filling is applied in the form of a string which has a width which corresponds at least substantially to the length of the finished tampon onto a strip of said layer material which has a greatest width exceeding the width of the string, said string being placed on the strip at least substantially symmetrically with the longitudinal centre line of said strip, wherein the strip of layer material having located thereon the string of absorbent material, for forming said tampon blank, is coiled onto a first tubular mandrel with said string located on the side of the strip facing towards said mandrel;

a part of the strip projecting from one side of the string with the end of the mandrel located adjacent the inner edge of said part is inserted into the interior of said first mandrel;

a second tubular mandrel is inserted through said mandrel end of the first mandrel in a manner such as to be surrounded by the layer-material part inserted into said first mandrel;

the first mandrel is then completely withdrawn;

a part of the strip projecting out from the string on the other side, with the end of the second mandrel located adjacent the inner end of said part, is inserted into the interior of the second mandrel; and the second mandrel is then fully withdrawn prior to compacting the tampon blank thus formed to its final tampon form.

8. A method according to claim 7, wherein the strip-part projecting out from said one side is inserted into said first mandrel by means of said second mandrel.

9. A method according to claim 7, wherein the strip-part projecting out from said other side is inserted into said second mandrel by means of a third mandrel.

10. A method according to claim 7, wherein a withdrawal thread is attached to the strip-part which projects out from said other side.

11. A method according to claim 10, wherein the strip-part to which the withdrawal thread is attached is drawn into the second mandrel by means of said withdrawal thread.

12. A method according to claim 7, wherein said material string is formed, at least partially, on the layer-material strip by supplying discrete particles or fibres of absorbent material to a region on one side of said strip and maintaining a subpressure in the same region on the opposite side of the strip.

13. A method according to claim 12, wherein at least an essential part of said absorbent material consists of defibrated paper pulp or fluff pulp.

14. A method according to claim 13, wherein said pulp is unbleached.

15. A method according to claim 7, wherein the material string is terminated at a distance from at least one end of the strip of layer material.

* * * * *